(12) United States Patent
Milenkovic

(10) Patent No.: US 9,031,699 B2
(45) Date of Patent: May 12, 2015

(54) KINEMATIC PREDICTOR FOR ARTICULATED MECHANISMS

(75) Inventor: Paul H. Milenkovic, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 310 days.

(21) Appl. No.: 13/567,881

(22) Filed: Aug. 6, 2012

(65) Prior Publication Data

US 2012/0303318 A1 Nov. 29, 2012

Related U.S. Application Data

(60) Provisional application No. 61/526,309, filed on Aug. 23, 2011, provisional application No. 61/521,449, filed on Aug. 9, 2011.

(51) Int. Cl.
  *G05B 19/41* (2006.01)
  *A61B 18/18* (2006.01)
  *A61B 18/00* (2006.01)

(52) U.S. Cl.
  CPC .............. *A61B 18/18* (2013.01); *A61B 18/1815* (2013.01); *A61B 2018/00023* (2013.01)

(58) Field of Classification Search
  CPC ............ B25J 9/00; B25J 9/003; G05B 19/05; G05B 19/042; G05B 19/0423; G05B 19/0426
  USPC ......... 700/245, 246, 250, 252, 253, 258, 259, 700/260, 261, 262, 263, 264; 318/568.11, 318/568.13, 568.14, 568.15, 568.16, 318/568.17, 568.18, 568.19, 568.2, 568.21, 318/568.22, 568.23
  See application file for complete search history.

(56) References Cited

U.S. PATENT DOCUMENTS

| | | | | |
|---|---|---|---|---|
| 4,887,222 | A * | 12/1989 | Miyake et al. | 700/262 |
| 5,206,930 | A * | 4/1993 | Ishikawa et al. | 700/260 |
| 5,767,648 | A * | 6/1998 | Morel et al. | 318/568.1 |
| 2003/0108415 | A1* | 6/2003 | Hosek et al. | 414/783 |
| 2004/0210426 | A1* | 10/2004 | Wood | 703/2 |
| 2005/0209534 | A1* | 9/2005 | Dariush | 600/595 |

OTHER PUBLICATIONS

Karmarkar et al.; Power Series Variants of Karmarkar-Type Algorithms; AT&T Technical Journal; May/Jun. 1989; pp. 20-36.*
Lloyd; Desingularization of Nonredundant Serial Manipulator Trajectories Using Puiseux Series; IEEE Transactions on Robotics and Automation; vol. 14, No. 4; Aug. 1998; pp. 590-600.*
Karsai, Geza, Method for the Calculation of the Combined Motion Time Derivatives of Optional Order and Solution for the Inverse Kinematic Problems, Mechanism and Machine Theory 36 (2001), pp. 261-272.

(Continued)

*Primary Examiner* — Stephen Holwerda
(74) *Attorney, Agent, or Firm* — Boyle Fredrickson, S.C.

(57) ABSTRACT

A predictor usable for rapid and accurate calculation of joint commands of an articulated mechanism describes relationship between the joints in the form of a differential equation. The predictor solves this differential equation by direct substitution of a power series for each of its variables and the combining of selected sets of coefficients of these power series into linear systems of equations which may be solved to determine power series coefficients to arbitrary order.

16 Claims, 7 Drawing Sheets

(56) References Cited

OTHER PUBLICATIONS

Ambike, Satyajit, et al, Geometric, Spatial Path Tracking Using Non-Redundant Manipulators via Speed-Ratio Control, Proceedings of the ASME 2010 International Design Engineering Technical Conferences & Computers and Information in Engineering Conference, Aug. 16-18, 2010, Montreal, Quebec, Canada.

Milenkovic, Paul, Series Solution for Finite Displacement of Planar Linkages, Journal of Mechanisms and Robotics, vol. 3, pp. 014501-1-014501-7, Feb. 2011.

* cited by examiner

KINEMATIC PREDICTOR FOR ARTICULATED MECHANISMS

CROSS REFERENCE TO RELATED APPLICATION

This application claims the benefit of U.S. provisional application 61/526,309 filed Aug. 23, 2011 and the benefit of U.S. provisional application 61/521,449 filed Aug. 9, 2011 both hereby incorporated by reference.

BACKGROUND OF THE INVENTION

The present invention relates to articulated mechanisms, such as but not limited to robot arms, and more particularly to a predictor for determining joint positions and rates for multiple joints based on a desired movement of one or more other joints, such as is necessary for control or design of articulated mechanisms.

Articulated mechanisms such as a robot arm can be understood as a set of rigid links connected to each other by joints. The joints for a robot arm may be associated with actuators such as motors to move the joints and sensors providing an indication of joint position. Common joints include so-called revolute joints acting like a hinge to provide rotation about an axis and prismatic joints acting like a slide to provide translation along an axis. These types of joints are termed "lower-pair joints". The absolute or global position of each joint is determined by the previous joints in the form of a kinematic chain where one joint is attached to and thus referenced to the "ground" which provides a global reference frame.

A typical robot arm, for example, might provide for six joints of various kinds describing six degrees of freedom. For example, a robot arm may swivel about a waist joint which supports a pivoting shoulder joint which in turn supports a pivoting elbow joint, which attaches to an extension for an arm joint allowing forearm rotation, in turn attaches to a pivoting and swiveling wrist joint the latter of which is attached to a tool such as an actuatable clamp, a paint sprayer, or welding gun, or any other such tool fixed to one link of that robot arm.

The position of the robot arm and its tool fixed to the terminal link may be readily calculated by using standard trigonometric formulas applied to each joint starting at the joint attached to ground to successively determine the locations and orientations of the later joints along with their intermediate links until the "effector" link is reached (sometimes but not always the last link in the chain). This calculation is termed the "forward kinematic" problem and requires knowledge of the axis values (e.g. joint angles) of each joint and of the structure of the mechanism (e.g. the link lengths, relative orientation of joints at each end of a link, types of joints etc.). This information, which describes the articulated mechanism, defines a "kinematic equation". The kinematic equation may be readily expressed in a matrix form such as the Denavit-Hartenberg (D-H) matrix. That D-H matrix fully characterizes the translation and orientation of a link in an articulated mechanism from a reference position.

An important robot control problem involves determining the angles or extensions of the various joints necessary to position the robot tool (effector) in a desired orientation and location. This is the so-called "inverse kinematics" problem and again requires finding a solution to the kinematic equation meeting the desired tool position. In one approach to the inverse kinematics problem, the kinematic equation is formed into a loop equation by adding a final fictitious joint connection between the tool link and the work surface fixed to ground so that the entire mechanism satisfies a closed-loop kinematic equation. That fictitious joint constrains the spatial motion to be taken by the tool over one segment of a desired robot work task. The desired tool positions and orientations at the start and end of that segment of the work task define the type, location, and movement range of this final fictitious joint.

Some industrial robots, especially those with a "spherical wrist" having the roll, yaw, and pitch axes intersecting on a common center, have a mathematically closed-form inverse kinematic solution. For other robots, especially those with a non-spherical wrist or incorporating redundant joints to achieve a high level of dexterity, determining motion of the effector as part of the inverse kinematics problem from this loop equation may be done by differentiating the loop equation to determine its local slope which may be used to estimate the necessary joint movements in a process roughly analogous to the Newton Raphson method. Determining higher derivatives of a complicated loop equation may be done symbolically with significant manual effort or with a symbolic algebra software package, but quickly becomes intractable owing to the rapid growth in the number of terms that precludes checking such symbolic expressions for correctness or their practical implementation in computer software.

SUMMARY OF THE INVENTION

The present invention provides a computerized predictor for rapidly determining control parameters for articulated mechanisms on an automatic basis with a high degree of precision. This predictor may be used for machine control or to model such mechanisms for design purposes.

Generally, the predictor employs a system of kinematic differential equations describing the articulated mechanism and whose solutions describe motion of rigid links connected by joints and forming closed kinematic loops. These equations are solved by direct substitution of the equation variables with multi-term power series expressions. Each closed kinematic loop establishes a linear relationship between power series coefficients of the same order which allows formation of a system of independent, linearly related equations, the latter solvable by well known automatic techniques. Accuracy approaching the limit of precision of the computer may thereby be obtained by extending the number of power series terms treated.

Specifically then, the invention provides a predictor system for an articulated linkage in which an electronic computer stores a system of differential equations describing a rate of change in a joint state of each joint. The differential equations are expanded with power series representations of the joint state variables and an input trajectory of at least one joint state variable for which a work joint is received. Multiple orders of coefficients of the power series representations of the state variables for joints are then determined by solving a system of linear equations to produce output data describing displacement of the joints necessary to produce the input trajectory of work joint. As used herein, the term "solving a linear system of equations" should be understood to mean solving a linear system of equations one or more times as may be required in the procedure to calculate the power series coefficients.

It is thus a feature of at least one object of the invention to provide a high speed inverse kinematics calculation engine, important in robot control and design that provides high precision motion data without manual symbolic differentiation and without the approximation errors associated with conventional numeric differentiation.

The values of the state variables for joints may be determined by solving a linear system of equations in an order-recursive fashion in which lower orders of the coefficients of the power series are computed to provide values for the computation of later orders of the power series.

It is thus a feature of at least one embodiment of the invention to provide an efficient calculation process that scales well with multiple power series coefficients (for greater accuracy) and multiple axes (for more complex mechanisms). Earlier calculations provide data needed in later calculations.

The power series representations include power series terms to at least three orders.

It is thus a feature of at least one embodiment of the invention to provide for high precision calculations involving multiple power series terms normally impractical with current systems.

The joints described by the system of differential equations may form a loop starting at the ground link and proceeding through one or more joints to a second link to ground.

It is thus a feature of at least one embodiment of the invention to convert the linkage into a closed loop form that will produce a set of linear equations that may be readily solved without manual input by an electronic computer.

The second link may be a virtual link that is not part of the articulated linkage.

It is thus a feature of at least one embodiment of the invention to permit the technique to be used with articulated linkages that do not naturally form closed loops.

The joint states may be parameters of joint screws defining an axis and pitch along the axis and the rate of change.

It is thus an object of the invention to provide a formalism that greatly simplifies the definition of the differential equations, the inputting of a desired joint trajectory and the intervening calculations.

Alternatively, the system of differential equations may specify Denavit-Hartenberg displacement matrices.

It is thus a feature of one embodiment of the invention to provide a technique broadly applicable to different numeric descriptions of an articulated linkage.

Each joint may include an actuator controllably changing a joint position and the outputs may be adapted to drive the actuators. Further, each joint may include a sensor sensing a joint position and the electronic computer may further execute the stored program to receive inputs from the sensors providing joint positions of the joints.

It is thus a feature of at least one embodiment of the invention to provide a high-speed predictor system useful for real-time robotic control as may be required for an anthropomorphic walking robot, an adaptive vehicle suspension system, or other application requiring the real-time prediction of kinematic variables.

The system may include a user input terminal providing an input and a display and the electronic computer may further execute the stored program to receive inputs from a user describing joint numbers, joint types and linkage types and to modify template equations according to those inputs of joint numbers, joint types and link types to generate the system of differential equations.

It is thus a feature of at least one embodiment of the invention to provide a predictor system that does not presuppose sophisticated mathematical understanding of articulated linkage but that can be employed by a general user to provide an automatic processing of this data.

These particular objects and advantages may apply to only some embodiments falling within the claims and thus do not define the scope of the invention.

DETAILED DESCRIPTION OF THE PREFERRED EMBODIMENT

Figure 1:
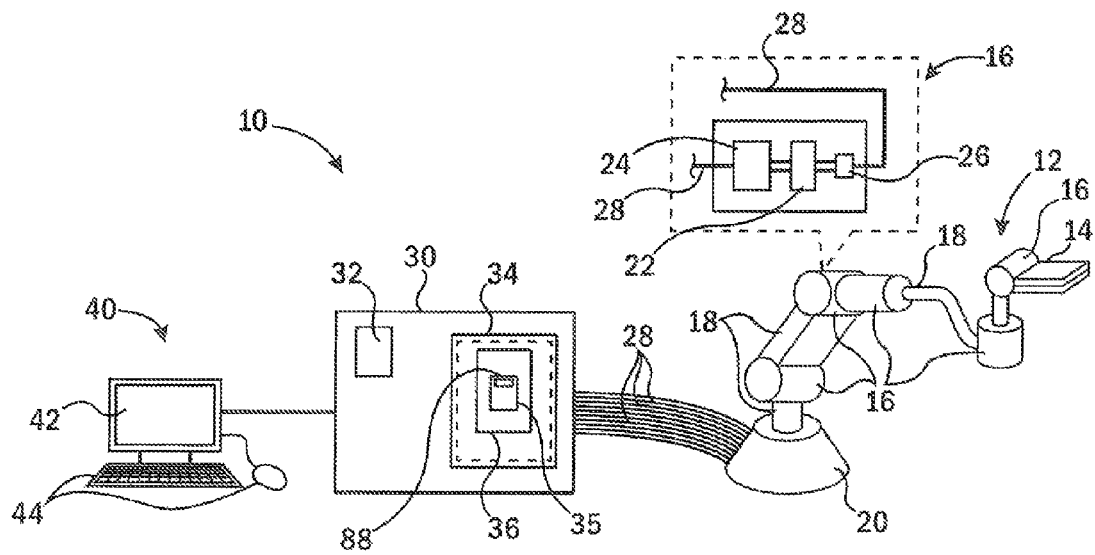
FIG. 1 is a simplified diagram of a an example robotic system having an articulated linkage of a type suitable for use with a joint movement predictor of the present invention, the robotic system associated with an electronic computer and user terminal.

Referring now to FIG. 1, a robot system 10 may include a robot arm providing an articulated linkage 12 having an end effector 14, for example, providing a tool such as a welder, paint gun, a device for grasping, or a supporting platform, or other application. The end effector 14 is connected by one or more joints 16 and links 18 to a base 20, for example, resting on a ground surface. Each of the joints 16 may include a joint mechanism 22, including but not limited to a slide or rotary coupling joining links 18 or one link 18 to the base 20 or to the end effector 14. Each of the joints 16 may communicate with an actuator 24, such as a motor for moving the joint 16, and a sensor 26, such as an encoder and/or tachometer, for reading out the position and velocity of the joint 16 when moved. Each link 18 provides a substantially rigid bar extending between two joints 16 or a joint 16 and the base 20.

Electrical signals to the actuators 24 and from the sensor 26 may be communicated over control lines 28 to an electronic computer 30. The electronic computer 30 may have a processor 32 communicating with a memory 34 such as random access memory, disk drive, or the like. The memory 34 may hold, among other programs such as an operating system, a predictor program 36 as will be described below. The memory 34 may further hold a mathematical description 38 of the articulated linkage 12 expressed in the form of a differential equation. The computer 30 may communicate with a user terminal 40 providing, for example, a display screen 42 which may display text and/or graphics and the user input device 44 such as a keyboard and mouse of types well known in the art.

Figure 2:
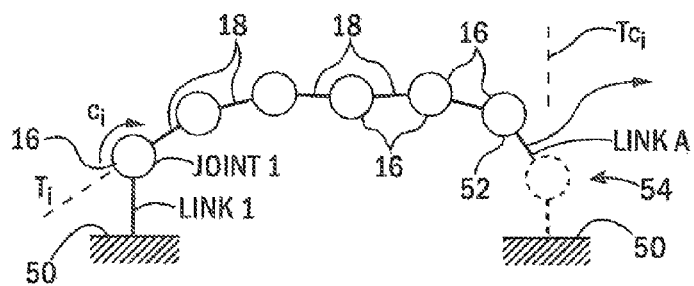
FIG. 2 is an abstract representation of an articulated linkage showing associated joint screw axes, instantaneous link screw axes, and joint rates, as well as a virtual joint for providing a loop closure of an otherwise unclosed articulated linkage.

Referring now to FIG. 2, the articulated linkage 12 of FIG. 1 may be abstracted as a chain of joints 16 having a joint type (e.g. revolute, prismatic, etc.) and links 18 having link parameters (e.g. length) extending from a ground reference 50. While a chain with a single path is shown in FIG. 2, the present invention is also applicable to linkages having parallel paths proceeding from branch points. The ground reference 50 provides a global reference frame but need not be physically attached or fixed with respect to the Earth.

In the notation used herein, the first link connected to the ground will be considered link 1 and the joint connected to that link will be considered joint 1 and so forth.

In the present invention, the chain provided by the articulated linkage 12 will be described mathematically as having the form of a closed linkage, meaning that the first and last joints (along some path through the joints and links) are both connected to ground. This closure may occur naturally in the articulated linkage 12 (for example, with the Stewart-Gough Platform) or may be forced through the definition of an additional virtual link and joint 54 as will be discussed below. One of the joints 16 may be designated as a work joint 52. The work joint 52 will be the joint 16 that defines the desired motion of the effector 14 and may be a final joint in the linkage, for example, the virtual joint 54 attached to the effector 14. More generally, any joint 16 or group of joints 16 may comprise the work joint 52 which are more generally the joints 16 which define the motion of a portion of the articulated linkage 12 intended to interact with some external device or application. As used herein, the term "work joint" should be understood to mean one or more work joints as the application would require.

For a linkage naturally in a closed form, the work joints 52 may be actual joints 16 not virtual joints 54. An example of a linkage where the effector is not the final link is a Stewart-Gough Platform, for example, as used in flight simulators and the like where intermediate joints in the chain support the platform.

Figure 3:
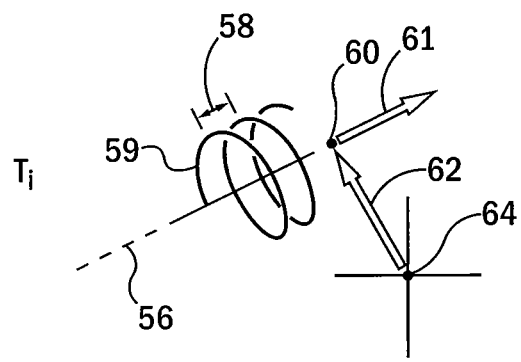
FIG. 3 is a perspective representation of a joint screw showing defining parameters.

Referring still to FIG. 2, the mathematical description of the articulated linkage 12 in a preferred embodiment may describe the position of each joint 16 as a mathematical screw $T_i$ where the subscript i represents the number of the joint 16 discussed above. Referring momentarily to FIG. 3, a mathematical screw provides for a screw axis 56 having a defined orientation in three-space and a pitch 58 describing the axial separation between periodic loops of a helical trajectory 59 around the axis 56. For a typical revolute joint, the pitch 58 will be zero and for a prismatic joint, the reciprocal of the pitch will be zero. The mathematical screw $T_i$ may be defined, for example, by Plucker coordinates providing for a vector 61 aligned with axis 56 (for example a unit vector defined by three scalars) and extending from an axis point 60 defined by three point coordinate scalars that may be visualized as the tip of a second vector 62 from a local origin 64 to the axis point 60.

Accordingly, six scalar values (a vector) fully characterize $T_i$. Generally each joint screw will be of the form:

$$T_i = (\omega_i; r_i \times \omega_i + h_i \omega_i) \quad (1)$$

where $\omega_i$ is the unit-magnitude direction vector 59 of the joint axis, $r_i$ is the point 60 selected along the joint axis line, and $h_i$ is the screw pitch of the joint. As noted before, $h_i=0$ for a revolute joint. For $h_i=0$, $T_i$ also gives the Plucker coordinates for the joint axis 56. Plucker coordinates, as is understood in the art and owing to properties of the vector cross product, provide a unique descriptor for a line, in contrast, for example, to the non-unique descriptors provided by two points on the line.

Referring, again to FIG. 2, each joint 16 may also be associated with a scalar joint rate $C_i$ for the joint 16 being a rate, for example, in angle along the trajectory 59 or a rate in distance along the axis for prismatic joints. The values of $T_i$ and $C_i$ provide state variables for each joint fully characterizing the articulated linkage 12 and the motion of its component links at a point in time.

Each link 18 is also associated with an instantaneous screw $T_{Ci}$ being a mathematical screw having a pitch and axis where the axis is not necessarily aligned with an actual joint axis but is the result of the combined motion of joints 16 connecting that link to ground reference. Generally, the instantaneous screw will be according to the form:

$$T_{Ci}(t) = (\omega_{Ci}(t); v_{C0i}(t)) = \sum_{j=1}^{i-1} C_j(t) T_j(t) \quad (2)$$

where $T_{Ci}(t)$ is the instantaneous screw for a given link 18, coefficients $C_j(t)$ give the scalar joint rates, and $T_j(t)$ gives the joint screws in global coordinates for each joint 16 along a path of connections to the given link 18 along the articulated linkage 12. Vector $\omega_{Ci}(t)$ is the angular velocity of the instantaneous link screw, where $\omega_{Ci}(t)/\|\omega_{Ci}(t)\|$ expresses the instantaneous rotation axis of a link and $\|\omega_{Ci}(t)\|$ the instantaneous rate of rotation about that axis, and $v_{C0i}(t)$ gives the velocity of the point on a hypothetical extension of the link that is coincident at time t with the coordinate origin. When the articulated linkage 12 is formed into a closed loop, as discussed above, equation (2) for link i=n+1 equals zero.

Figure 4:
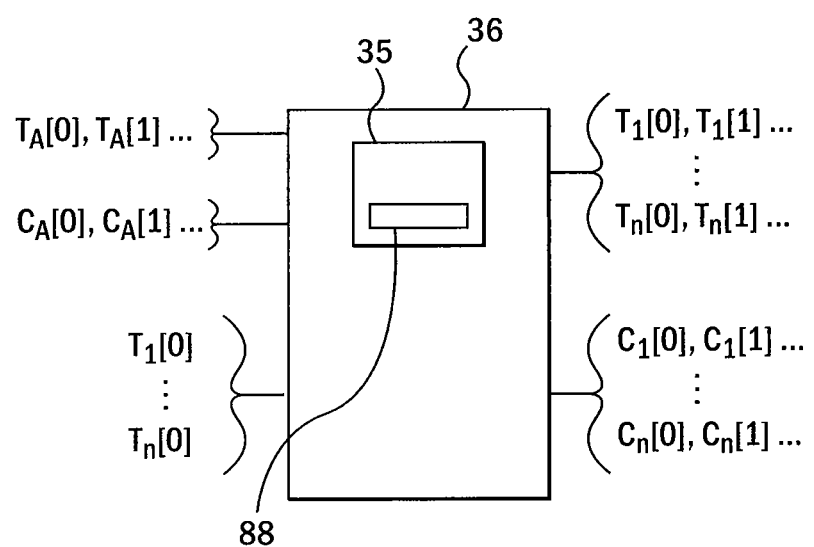
FIG. 4 is a fragmentary view of a display screen associated with the terminal of FIG. 1 showing a menu driven input system allowing the user to automatically generate the necessary system of differential equations.

Referring now to FIG. 4, the predictor program 36 as implemented in software in the computer 30 may receive information about a desired screw $T_A$ of a given work joint A and a desired motion $C_A$ of that work joint A, both expressed as a power series having terms [0], [1], . . . as will be discussed below. In the case of an joint connected to ground having a constant screw, the higher order terms $T_A[1]=0$, $T_A[2]=0$, . . . . The work joint will be termed an "active joint". Generally the invention is not limited to a single active joint but the orientations and desired motions of multiple active joints may be input. In addition, the predictor program 36 will receive initial positions of the joints other than the work joint in the form of the zero order terms $T_1[0]$, . . . , $T_n[0]$ which may be passed through to the outputs, the predictor program 36 adding higher order terms.

The predictor program 36 will then output descriptions of the positions and motions of all of the other joints (termed passive joints) again expressed as positions of screw axes of the given joints $T_i$ and motions $C_i$ of the given joints (typically from joint 1 to n exclusive of the work joint where n is the highest joint number). As with the inputs, these outputs will normally be in the form of a power series having multiple terms, of order that can exceed the supplied number of terms of the inputs by deeming higher order terms of the inputs to be zero-valued. The present invention simplifies the process of calculating these outputs so that power series terms in excess of three may be readily obtained automatically with reasonable computation times. As a general matter, this inverse calculation allows a desired motion of the effector 14 to be input in a command signal, and the necessary motions of all of the other joints needed to produce the desired motion of the effector 14 to be rapidly calculated and output to control a robot or the like.

Referring to FIGS. 1 and 4, as an initial step, the predictor program 36 requires a kinematic model 35 of the articulated linkage 12 (shown in FIG. 1) in order to make this inverse calculation. This kinematic model 35 is in the form of a series of differential equations of a closed loop of the articulated linkage 12 and may be automatically entered by the user from simple parameters.

Figure 5:
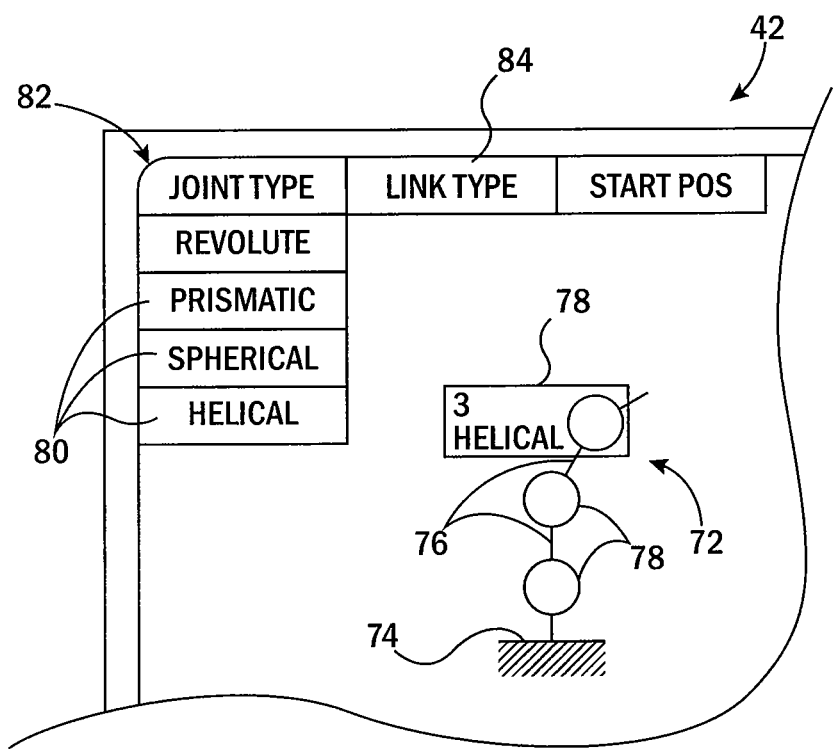
FIG. 5 is a block diagram showing input and output data to the predictor of the present invention for an inverse kinematics solution.
Figure 6:
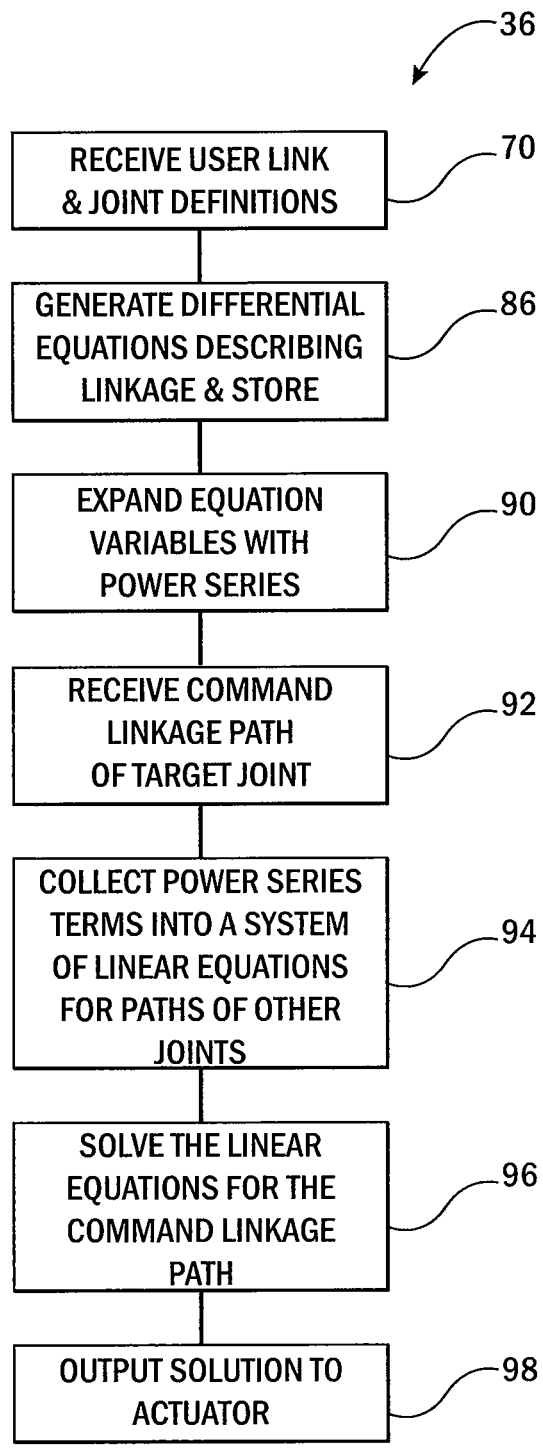
FIG. 6 is a flowchart showing the principal steps of the present invention as executed on an electronic computer.

Referring now also to FIGS. 5 and 6, in a first step of the process of the predictor program 36, as indicated by process block 70, the electronic computer 30 may receive through the terminal 40 a description of the articulated linkage 12 to produce the kinematic model 35. In one embodiment, the user may be guided through the creation of a graphic representation 72 of the articulated arm roughly analogous to that shown in FIG. 2 of the present invention providing a ground reference symbol 74 and multiple link symbols 76 connected by multiple joint symbols 78. The user may add the joint symbols 78 one at a time starting at the ground reference symbol 74. For example, using a menu-driven structure, the user may select a joint type from a number of different joint types 80 listed in a joint menu 82, for example, including revolution, prismatic, spherical, and helical joints. Each of these joint types may be represented by the screw formalism described above in the kinematic model 35. So, for example, the user may invoke a command to add a new joints symbol 78 providing a highlighted joints symbol 78' and may define the joint type at that time. In a similar process, a link menu 84 may be invoked to describe the parameters of the links 18 associated with link symbols 76 as may be added by similar steps. Generally the links 18 will have a parameter of length and orientation with respect to the screws of the joint symbols 78.

Per process block 86 of FIG. 6, this entered data may be used to generate a differential equation system for the kinematic model 35 from templates (implicit in the predictor program 36) populated by the user-entered description of number of joints, types of joints 16, and types of links 18 captured in a data file 88 (shown in FIG. 4). Generally the differential equation systems of the kinematic model 35 will be of the form:

$$\dot{T}_i(t) = T_{Ci}(t) \times T_i(t). \quad (3)$$

The × symbol operating on 6-element vectors denotes the Lie product, also known as the Lie bracket on the Lie algebra for instantaneous screws in Euclidean 3-space. That symbol is the boldface counterpart to the ordinary vector cross product symbol × operating on 3-element vectors. Expressing Eq. (3) in terms of component vector cross products gives:

$$(\dot{\omega}_i(t); \dot{v}_{0i}(t)) = (\omega_{Ci}(t) \times \omega_i(t); \omega_{Ci}(t) \times v_{0i}(t) - \omega_i(t) \times v_{C0i}(t)). \quad (4)$$

Equation (4) is a formula for the derivative for a joint screw. The interpretation of Eq. (4) as a kinematic differential equation is believed to be new to the invention, where the solution of that differential equation gives the spatial path taken by the joint axis line screw in response to the instantaneous screw (combined angular and translational velocity) of its connecting link.

The user-entered data of data of the data file 88 entered per process block 70 of FIG. 6 may be used to generate a differential equation system using equations (2) and (3) on an automatic basis without significant human intervention. The number of joints defines the allowed range of the index j in equation (2) and the joint definitions defining the screw parameters of the joints.

Referring now to FIG. 6 and process block 90, the variables of the system of linear differential equations may then be directly replaced with power series representations of the type shown in FIG. 4 as follows:

$$C_i(t) = C_i[0] + C_i[1]t + C_i[2]t^2 + $$

$$T_i(t) = T_i[0] + T_i[1]t + T_i[2]t^2 + $$

$$T_{Ci}(t) = T_{Ci}[0] + T_{Ci}[1]t + T_{Ci}[2]t^2 + \quad (5)$$

At process block 92, the desired command signal describing a desired control of the articulated linkage 12 may be received. In a preferred embodiment of the present invention, this real-time command is expressed as a trajectory of the effector 14 by definition of movement of virtual joint 54 (as shown in FIG. 2) or other joint 16 attached to the effector. The virtual joint 54 will often provide a simpler definition of the desired effector motion because it is attached to ground. When complex motions are required, the trajectory may be expressed piecewise as the motion and position of a sequence of virtual joints 16. As noted with respect to the discussion of FIG. 4, this command signal input may be provided in the form of the power series coefficients to match the expression of the other variables in the differential equation. For a constant rate of motion about a fixed virtual joint axis, that power series has non-zero terms for index k=0 along with zero values for the higher power series terms.

Referring again to FIG. 6, in process block 94 the system of closed kinematic loops described by the differential equations of the kinematic model 35 allows power series terms for each variable of the differential equations to be collected into a set of linear equations that may be solved per process block 96 for joints i (as expressed by power series terms) to provide the desired motion of joint A. Generally, the same linear closure equation will apply to each term of the power series and by processing these equations in power series term order, the results of earlier computations may be reused for the later complications significantly decreasing computational time. This process of forming the linear equations and their solution is discussed further below in Example I.

As indicated by process block 98 and referring to FIG. 4, output values describing each of the passive joints may then be provided to the robot to make the necessary controls of those joints to produce the desired trajectory of the effector joint working.

Example I

Figure 7:
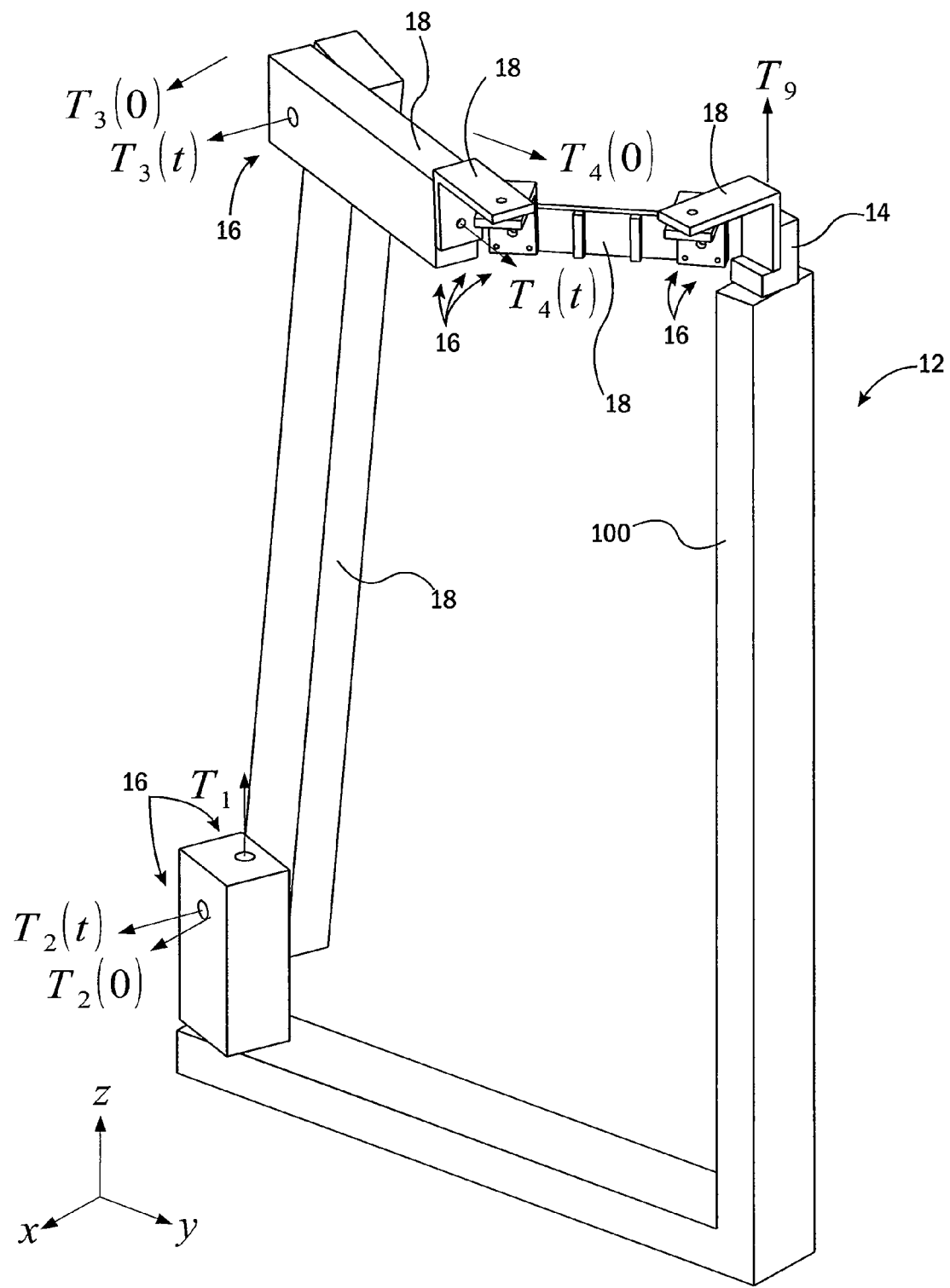
FIG. 7 is a perspective view of a second articulated linkage showing joint screw axes and a virtual joint screw axis as will be used in an example of the invention.

Referring now to FIG. 7, an example articulated linkage 12 is shown providing 8 joints 16 (only joints 1-4 labeled for clarity) and associated links 18. A final effector 14 rests on top of a workpiece 100 and may, for example, be commanded to move in a circular trajectory on an upper face of the workpiece 100 to provide a polishing motion. This command may be expressed as a simple motion of a virtual ninth joint. The screw axes having initial positions $T_i = T_i(0)$ and changing dynamically as $T_i(t)$ over time t are depicted.

Figure 8:
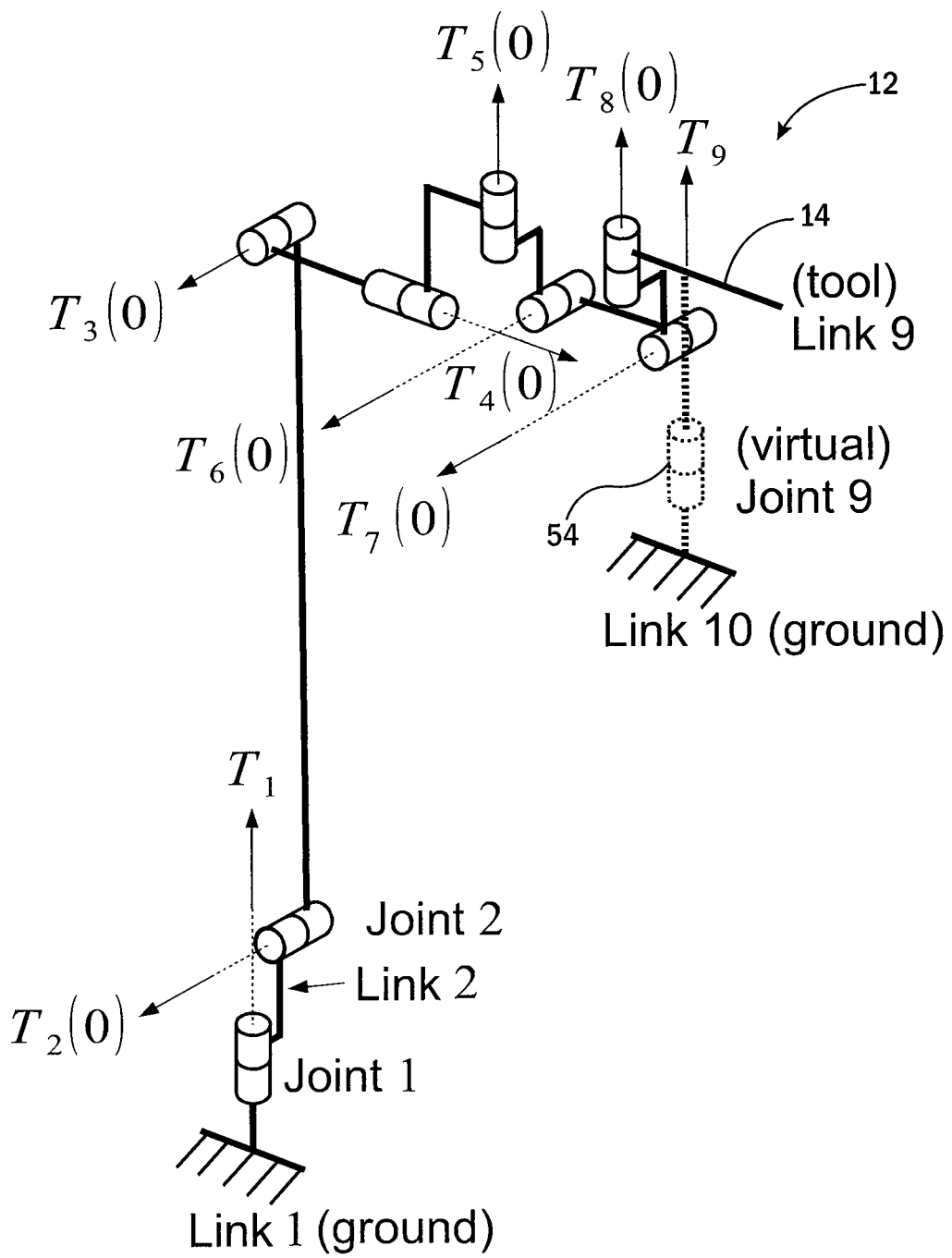
FIG. 8 is diagrammatic representation of the articulated linkage of FIG. 7 with a full labeling of the joint screw axes.
Figure 9:
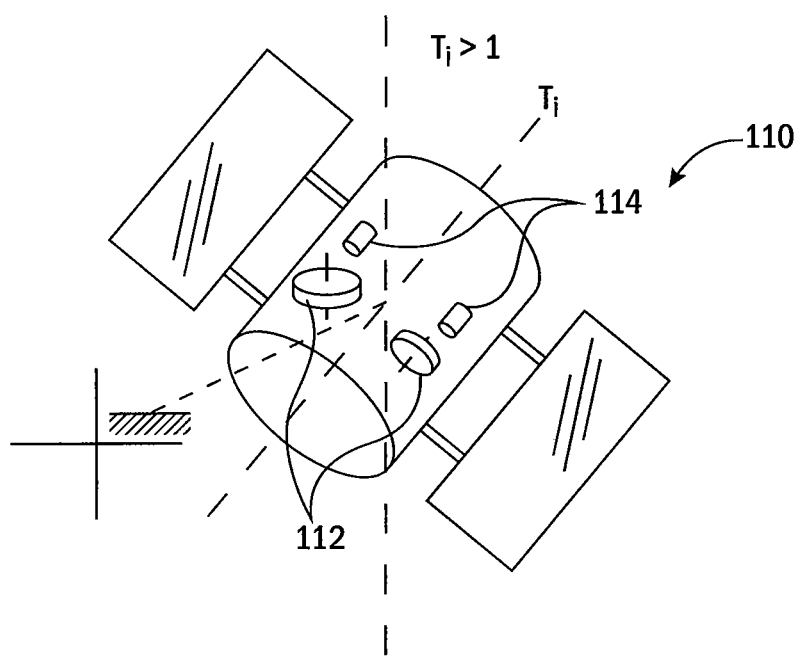
FIG. 9 is a simplified representation of a spacecraft presenting a control problem formulated as an articulated linkage such as may be addressed by the present invention.

This same mechanism is abstracted in FIG. 8 to fully label each axis and to show the ninth virtual joint 54 that may, for example, define a simple circular polishing motion of the effector 14 attached to the virtual joint 54. Virtual joint 54 further closes the articulated linkage 12.

The following process solves a closed kinematic loop for power series coefficients of the "passive" subset of joint rates $C_i$ (index i restricted to those passive joints, e.g. 1-8) when supplied with the input parameters of a command signal for the "active" subset of joint rates $C_i$ (index i restricted to those active joints, e.g. 9), also known as the rates of the work joint comprised of at least one work joint. Among the "passive" subset of joint rates, the relations $C_8 = C_5$ and $C_7 = C_6$ effect the motions of a known type of robotic wrist with a large range of motion. The joint-rate power series coefficients for the ninth joint are supplied as input parameters per FIG. 4.

It will be understood that this process can be extended to multi-loop linkages upon identifying all loops, which is done by known graph-search algorithms, and by augmenting a linear system of equations to include the linear relationships among all loops.

(1) Initial Inputs

Initial joint screws $T_i$ giving initial series coefficients $T_i = T_i[0]$ for all joints, series coefficients $C_9[k]$ for the one active joint on the coefficient-index range $0 \le k \le p-1$ provide the command inputs. Index p designates the requested upper order of the series coefficients. The kinematic loop has joints $1 \le i \le n$ and links $1 \le i \le n+1$ where n=9. Links 1 and n+1 are fixed in relation to ground reference whereas links $2 \le i \le n$ are movable. The initial joint screws may be calculated from initial direction vectors and points from anywhere along the joint axis lines:

$$T_i = (\omega_i;\ r_i \times \omega_i + h_i \omega_i) \text{ or } T_i = (0;\ \omega_i) \quad (6)$$

where the second formula in Eq. (6) is specific to a prismatic joint where the first formula is scaled by $1/h_i$ and then $1/h_i$ is set to zero. The initial joint direction vectors $\omega_i$ and axis points $r_i$ may in turn be specified from initial joint angles $\theta_i$, that may be input from sensors, together with link lengths and joint orientations in relation to their connecting links, supplied to known formulas for calculating geometric relationships.

(2) Repeated Step

The process performs the following calculations for successive index values in the range $0 \le k \le p-1$ to determine passive joint rate coefficients $C_i[0]$ through $C_i[p-1]$ and all joint screw coefficients $T_i[1]$ through $T_i[p]$. First, it calculates power series coefficients for the instantaneous link screws $$T_{Ci}(t) = \sum_{j=1}^{i-1} C_j(t) T_j(t),$$

performing that calculation for the power series coefficients of the product of two power series with the Cauchy product formula, but without terms of the form $C_i[k]T_i[0]$, which are excluded at this stage because the coefficients $C_i[k]$ are not yet known. Such coefficients labeled $T_{BCi}[k]$ are computed by excluding the m=k terms in the following summations according to:

$$T_{BC2}[k] = \sum_{m=0}^{k-1} C_1[m] T_1[k-m]; \quad (7)$$

$$T_{BCi}[k] = T_{BCi-1}[k] + \sum_{m=0}^{k-1} C_{i-1}[m] T_{i-1}[k-m],\ 3 \le i \le n;$$

$$B[k] = T_{BCn+1}[k] = T_{BCn}[k]$$

When k=0, this formula is defined to evaluate to $T_{BCi}[0]=0$, $2 \le i \le n+1$ giving B[0]=0. That $T_{BCn+1}[k]=T_{BCn}[k]$ follows from series coefficients $T_n[k]=0$ for $k \ge 1$, which is a consequence of joint n being fixed at ground reference and hence having the constant joint screw $T_n(t)=T_n[0]$. Coefficients $T_1[k]=0$ for $k \ge 1$ as $T_1(t)=T_1[0]$ follows from the first joint also being at ground reference.

Next, the process restores the m=k upper limit to the summations in Eq. (7) to reintroduce the $C_i[k]T_i[0]$ terms, where coefficients $C_i[k]$ for the passive joints are now treated as unknowns in a linear relationship. Applying the loop closure condition $T_{Cn+1}(t)=0$ leads to the linear system:

$$AC[k] + B[k] = 0 \quad (8)$$

which is solved for the passive $C_i[k]$ coefficients given the active $C_i[k]$. The columns of constant matrix A=A[0] are the initial joint screws $T_i$ (and the rows are the six elements of the $T_i$ vectors) and vector C[0] has elements $C_i[0]$. The factorization of a matrix comprised of the passive-joint columns of A need only be performed once, and subsequent solutions to the linear system of equations can be obtained by supplying different right-hand side vectors B[k] to that factorization.

After solving the preceding system of linear equations for $C_i[k]$, calculate $$\Sigma_1 = C_1[k] T_1[0];$$

$$\Sigma_{i-1} = \Sigma_{i-2} + C_{i-1}[k] T_{i-1}[0],\ 3 \le i \le n; \quad (9)$$

$$T_{Ci}[k] = \Sigma_{i-1} + T_{BCi}[k],\ 2 \le i \le n$$

Coefficient values $T_{Ci}[k]$ for the instantaneous screws are computed in this way for all movable links as the instantaneous screws may be used to compute other kinematic variables or to compute forces acting on the links. Coefficient values $T_i[k+1]$ for the joint screws, however, only need to be computed for those joints not connected directly to ground. The power-series solution of the screw kinematic differential equation leads to calculating:

$$T_i[k+1] = \frac{1}{k+1} \sum_{m=0}^{k} T_{Ci}[m] \times T_i[k-m],\ 2 \le i \le n-1 \quad (10)$$

where boldface × denotes the Lie product operator for 6-element twist vectors (also called the Lie bracket).

(3) Outputs

The preceding process generates power series coefficients for joint rates $C_i[0], \ldots, C_i[p-1]$ and joint screws $T_i[0], \ldots, T_i[p]$. The joint rate values:

$$C_i(t) = C_i[0] + C_i[1]t + C_i[2]t^2 + \ldots + C_i[p-1]t^{p-1} \quad (11)$$

form an inverse kinematic solution used to control a robot to achieve the designated work task. High accuracy can be maintained by starting at time t=0 and ending at t=h, by computing joint screws $$\begin{aligned} T_i(h) = &T_i[0] + T_i[1]h + T_i[2]h^2 + \ldots + \\ &T_i[p-1]h^{p-1} + T_i[p]h^p \end{aligned} \quad (12)$$

and then using $T_i(h)$ as new values for the joint screws $T_i(0) = T_i[0]$ at the start of a new time interval.

Additional discussion and explanation of these methods are described in the papers, Milenkovic, P., 2012, "Series Solution for Finite Displacement of Single-Loop Spatial Linkages," Journal of Mechanisms in Robotics, ASME, vol. 4 (pp. 021016-1:8) and Milenkovic, P., 2011, "Solution of the Forward Dynamics of a Single-Loop Linkage Using Power Series," Journal of Dynamic Systems, Measurement, and Control, ASME, vol. 133 (pp. 0610021:9) both by the present inventor and both incorporated by reference in their entirety.

Referring now to FIG. 8, it will be appreciated that the concept of articulated linkage may be generalized to include, for example, structures such as a spacecraft 110 rotatable about axes $T_i$ orthogonal axes relative to the center of mass of spacecraft 110 acting like a joint. In this case the ground link may be conceptual to a desired ground reference, for example, a point in an orbiting reference. In this embodiment, actuators may be reaction wheels 112 and the sensors may be, for example, gyroscopes or inertial sensors 114 and the solutions provided by the predictor of the present invention used for orientation and guidance of the spacecraft 110.

It will be understood that the invention described herein may also be applied to the control of objects whose motion can be decomposed into specific axes but where one or more of the links may represent conceptual rather than actual structure, for example, in the control of spacecraft with respect to the Earth where there is no physical link to the Earth.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What I claim is:

1. A predictor system comprising:
    an articulated linkage providing a system of links connected by joints including at least one ground link referenced to a global ground reference;
    an electronic computer executing a. stored program held in non-transitory media to:
    (1) store at least two systems of differential equations, a first system describing a rate of change in joint states as a function of other joint states, and a second system accounting for continuous changes in that function as the linkage articulates, wherein the joints are held as joint state variables, and wherein the joints include at least one work joint;
    (2) expand the joint state variables with power series representations of the joint state variables;
    (3) receive an input describing a trajectory of at least one joint state variable of the at least one work joint;
    (4) determine values of multiple orders of coefficients of the power series representations of the state variables for joints other than the at least one work joint satisfying a linear relationship among power series coefficients for the state variables; and
    (5) output data describing displacement of the joints other than the at least one work joint necessary to produce the input trajectory of the joint state variable of the at least one work joint;
    wherein each joint includes an actuator controllably changing a joint position providing and wherein the outputs are adapted to drive the actuators.

2. The predictor system of claim 1 wherein the values of multiple orders of coefficients of the power series representations of the state variables for joints other than the at least one work joint are determined by solving a linear system of equations in an order-recursive fashion in which lower orders of the coefficients of the power series are computed to provide values for a computation of later orders of the power series.

3. The predictor system of claim 2 wherein the electronic computer further executes the program to solve the systems of differential equations in order-recursive fashion so that determining the coefficients of the linear system of equations unique to the next order uses a non-zero, finite and constant number of additional calculation steps over the number of calculation steps used when determining the coefficients unique to the current order.

4. The predictor system of claim 3 wherein the joints described by the system of differential equations form a loop starting at the ground link and proceeding through one or more joints to a second link to ground.

5. A predictor system comprising;
    an articulated linkage providing a system of links connected by joints including at least one ground link referenced to a global ground reference;
    an electronic computer executing a stored program held in non-transitory media to
    (1) store a system of differential equations describing a rate of change in a joint state, each joint as a function of other joint states, the joint states describing positions of the joints and held as joint state variables where the joints include at least one work joint;
    (2) expand the joint slate variables of the sestet of differential equations with power series representations of the joint state variables;
    (3) receive an input describing a trajectory of at least one joint state variable of the at least one work joint;
    (4) determine values of multiple orders of coefficients of the power series representations of the state variables for joints other than the at least one work joint satisfying a linear relationship among power series coefficients for the state variables; and (5) output data describing displacement of the joints other than the at least one work joint necessary to produce the input trajectory of the joint state variable of the at least one work joint;

wherein each joint includes an actuator controllably changing a joint position providing a joint state and wherein the outputs are adapted to drive the actuators;

wherein the values of multiple orders of coefficients of the power series representations of the state variables for joints other than the at least one work joint are determined by solving a linear system of equations in an order-recursive fashion in which lower orders of the coefficients of the power series are computed to provide values for a computation of later orders of the power series;

wherein the power series representations include power series terms to at least three orders;

wherein the joints described by the system of differential form a loop starting at the ground link and proceeding through one or more joints to a second link to ground; and wherein the second link is a virtual link that is not part of the articulated linkage.

6. The predictor system of claim 4 wherein the joint states are parameters of joint screws defining an axis and pitch along the axis and the rate of change.

7. The predictor system of claim 6 wherein the input trajectory is expressed as a rate of change of the at least one work joint.

8. The predictor system of claim 6 wherein the output provides a time history of joint screws of the joints other than the at least one work joint.

9. The predictor system of claim 6 wherein the system of differential equations is comprised of elements:

$$\dot{T}_i(t) = T_{Ci}(t) \times T_i(t)$$

where:
× is a Lie product;
i is an index for the joints;
the initial conditions to the differential equation are of the form
$T_i = (\omega_i; r_i \times \omega_i + h_i \omega_i)$ that provides a description of joint axis in Plücker coordinates;

$$T_{Ci}(t) = (\omega_{Ci}(t); v_{C0i}(t)) = \sum_{j=1}^{i-1} C_j(t) T_j(t)$$

and $C_j$ is a rate of motion in relationship to an axis.

10. The predictor system of claim 4 wherein the system of differential equations specifies Denavit-Hartenberg displacement matrices.

11. The predictor system of claim 1 wherein each joint includes a sensor sensing a joint position and wherein the electronic computer further executes the stored program to receive inputs from the sensors providing joint positions of the joints.

12. The predictor system of claim I further including a user input terminal providing an input and a display and wherein the electronic computer further executes the stored program to receive inputs from a user describing joint numbers, joint types and linkage types and to modify template equations according to those inputs of joint numbers, joint types and link types to generate the system of differential equations.

13. A method of controlling motion of an articulated linkage, the articulated linkage providing a system of links connected by joints including at least one ground link referenced to a global ground reference, the method comprising the steps of executing a program stored in non-transitory medium on an electronic computer to:

(1) store at least two systems of differential equations a first system describing a rate of change in joint states as a function of other joint states, and a second system accounting for continuous changes in that function as the linkage articulates, wherein the joints are held as joint state variables, and wherein the joints include at least one work joint;

(2) expand the joint state variables with power series representations of the joint state variables;

(3) receive an input describing a trajectory of at least one joint state variable of the at least one work joint;

(4) determine values of multiple orders of coefficients of the power series representations of the state variables for joints other than the at least one work joint satisfying a linear relationship among power series coefficients for the state variables; and (5) output data describing displacement of the joints other than the at least one work joint necessary to produce the input trajectory of the joint state variable of the at least one work joint;

wherein each joint of the articulated linkage includes an actuator controllably changing a joint position and further including the step of communicating how the output are adapted to drive the actuators; and wherein each joint further includes a sensor sensing a joint position and further including the step of receiving inputs from the sensors providing joint positions of the joints.

14. The method of claim 13 wherein the values of multiple orders of coefficients of the power series representations of the state variables for joints other than the at least one work joint are determined by solving a linear system of equations in an order-recursive fashion in which lower orders of the coefficients of the power series are computed to provide values for a computation of later orders of the power series.

15. The method of claim 14 the electronic computer further executes the program to solve the systems of differential equations in order-recursive fashion so that determining coefficients of the linear system of equations unique to the next order uses a non-zero, finite and constant number of additional calculation steps over the number of calculation steps used when determining the coefficients unique to the current order.

16. The method of claim 15 wherein the joints described by the system of differential equations form a loop starting at the ground link and proceeding through one or more joints to a second link to ground.

* * * * *